US012023365B2

(12) United States Patent
Bharate et al.

(10) Patent No.: US 12,023,365 B2
(45) Date of Patent: Jul. 2, 2024

(54) SUSTAINED RELEASE FORMULATIONS OF CROCUS SATIVUS

(71) Applicant: COUNCIL OF SCIENTIFIC & INDUSTRIAL RESEARCH, New Delhi (IN)

(72) Inventors: Sonali Sandip Bharate, Jammu (IN); Vikas Kumar, Jammu (IN); Rohit Singh, Jammu (IN); Sarita Rani, Jammu (IN); Mehak Gupta, Jammu (IN); Ajay Kumar, Jammu (IN); Sandip Bibishan Bharate, Jammu (IN); Ram Vishwakarma, Jammu (IN)

(73) Assignee: COUNCIL OF SCIENTIFIC & INDUSTRIAL RESEARCH, New Delhi (IN)

(*) Notice: Subject to any disclaimer, the term of this patent is extended or adjusted under 35 U.S.C. 154(b) by 304 days.

(21) Appl. No.: 16/753,969

(22) PCT Filed: Oct. 18, 2018

(86) PCT No.: PCT/IN2018/050629
§ 371 (c)(1),
(2) Date: Apr. 6, 2020

(87) PCT Pub. No.: WO2019/077621
PCT Pub. Date: Apr. 25, 2019

(65) Prior Publication Data
US 2020/0390843 A1 Dec. 17, 2020

(30) Foreign Application Priority Data

Oct. 16, 2017 (IN) .............................. 201711036684

(51) Int. Cl.
*A61K 9/16* (2006.01)
*A61K 36/88* (2006.01)
*A61P 25/28* (2006.01)

(52) U.S. Cl.
CPC ............ *A61K 36/88* (2013.01); *A61K 9/1635* (2013.01); *A61K 9/1652* (2013.01); *A61P 25/28* (2018.01); *A61K 2236/333* (2013.01)

(58) Field of Classification Search
None
See application file for complete search history.

(56) References Cited

U.S. PATENT DOCUMENTS

| 9,833,489 B2 * | 12/2017 | Bourges | A61P 3/00 |
| 2005/0208156 A1 * | 9/2005 | Ploch | A61K 2300/00 424/728 |
| 2009/0246276 A1 * | 10/2009 | Jackson | A61K 31/554 424/465 |
| 2014/0141082 A1 | 5/2014 | Gao | |
| 2016/0361272 A1 * | 12/2016 | Thomaoglou | A61K 31/455 |

FOREIGN PATENT DOCUMENTS

| CN | 1123663 A1 | 6/1996 | |
| CN | 103484960 B * | 6/2015 | ............... D01D 1/02 |
| CN | 106109523 A * | 11/2016 | ........... A61K 31/194 |
| WO | WO 2006066389 A1 * | 6/2006 | ............... B01J 13/00 |

OTHER PUBLICATIONS

Rahaiee et al., Improvement of crocin stability by biodegradable nanoparticles of chiotosn-alginate, International Journal of Biological Macromolecules, 70:423-432. (Year: 2015).*
Wang et al. Moisture adsorption and desorption properties of colloidal silicon dioxide and its impact on layer adhesion of a bilayer tablet formulation. J. Excipients and Food Chemistry. 5(1). p. 21-31. Mar. 2014 (Year: 2014).*
Nikbakht-Jam I et al, "Effect of crocin extracted from saffron on pro-oxidant-anti-oxidant balance in subjects with metabolic syndrome: A randomized, placebo-controlled clinical trial", European Journal of Integrative Medicine, Elsevier, Amsterdam, NL, vol. 8, No. 3, Dec. 23, 2015 (Dec. 23, 2015), p. 307-312.
Sonali S. Bharate et al, "Preclinical Development of Crocus sativus-Based Botanical Lead IIIM-141 for Alzheimer's Disease: Chemical Standardization, Efficacy, Formulation Development, Pharmacokinetics, and Safety Pharmacology", ACS Omega, vol. 3, No. 8, Aug. 20, 2018 (Aug. 20, 2018), p. 9572-9585.
F Hadizadeh, "Extraction and Purification of Crocin from Saffron Stigmas Employing a Simple and Efficient Crystallization Method", Pakistan Journal of Biological Sciences, vol. 13, No. 14, Jan. 1, 2010 (Jan. 1, 2010), p. 691-698.
J.L. Rios, An Update Review of Saffron and its Active Constituents, Phytotherapy Research, vol. 10, 189-193 (1996).
Hossein Hosseinzadeh, and Hani M. Younes, Antinociceptive and anti-inflammatory effects of Crocus sativus L.stigma and petal extracts in mice, BMC Pharmacology, 2: 7, Mar. 15, 2002 (Mar. 15, 2002).
J. Escribano et al., Crocin, safranal and picrocrocin from saffron (Crocus sativus L.) Inhibit the growth of human cancer cells in vitro Cancer Letters, vol. 100, pp. 23-30, (1996).
Fi Abdullaev, Biological Effects of Saffron Biofactors, 4(2): Apr. 30, 1993 (Apr. 30, 1993), pp. 83-86.
Hossein Hosseinzadeh and Vahid Khosravan, Anticonvulsant Effects of Aqueous and Ethanolic Extracts of Crocus Sativus L. Stigmas in Mice Archives of Iranian Medicine vol. 5(1), Jan. 2002 (Jan. 2002), pp. 44-47.
Hosseinzadeh, et al., Protective effect of aqueous saffron extract (Crocus sativus L.) and crocin, its active constituent, on renal ischemia-reperfusion-induced oxidative damage in rats Journal of Pharmacy and Paharmaceutical Sciences, 8(3), Aug. 22, 2005 (Aug. 22, 2005), pp. 39=87-393.

(Continued)

*Primary Examiner* — Lakshmi S Channavajjala
(74) *Attorney, Agent, or Firm* — Blank Rome LLP

(57) ABSTRACT

The present invention is related to the novel oral dosage form for sustained release of crocin-1, a active constituent of Crocus sativus extract or fraction and a process for preparing the same wherein the extract is wet-granulated using excipients, biodegradable polymers and/or non-biodegradable polymers alone or in combination. The said formulations are useful for the treatment of chronic inflammatory diseases wherein NLRP3 inflammasome is involved.

15 Claims, 5 Drawing Sheets

(56) References Cited

OTHER PUBLICATIONS

Abe et al, Saffron extract prevents acetaldehyde-induced inhibition of long-term potentiation in the rat dentate gyrus in vivo Brain Research 851 (1999), pp. 287-289.

Zhang et al., Effects of *Crocus sativus* L. on the Ethanol-Induced Impariment of Passive Avoidance Performances in Mice Biol. Pharm. Bull. 17(2) (1994) pp. 217-221.

Khalili et al., Behavioral and Histological Analysis of Crocus Sativus Effect in Intracerebroventricular Streptozotocin Model of Alzheimer Disease in Rats Iranian Journal of Pathology 5(1) (2010) pp. 27-35.

Papandreou et al., Inhibitory Activity on Amyloid-beta Aggregation and Antioxidant Properties of Crocus sativus Stigmas Extract and Its Crocin Constituents Journal of Agricultural and Food Chemistry, Oct. 2, 540, 2006 (Oct. 20, 2006), pp. 8762-8768.

Batarseh et al., Crocus sativus Extract Tightens the Blood-Brain Barrier, Reduces Amyloid β Load and Related Toxicity in 5XFAD Mice ACS Chem Neurosci. 8(8) Aug. 16, 2017 (Aug. 16, 2017) pp. 1756-1766.

Tarantilis et al., Determination of saffron (*Crocus sativus* L.) components in crude plant extract using high-performance liquid chromatography-UV-visible photodiode-array detection-mass spectrometry Journal of Chromatography A 699 (1995) pp. 107-118.

Pfister et al., Isolation and Structure Elucidation of Carotenoid-Glycosyl Esters in Gardenia Fruits (*Gardenia jasminoides Ellis*) and Saffron (*Crocussativus Linne*) Journal of Agricultural and Food Chemistry. 44 (9), (1996) pp. 2612-2615.

Carmna et al., Crocetin Esters, Picrocrocin and Its Related Compounds Present in Crocus sativus Stigmas and Gardenia jasminoides Fruits. Tentative Identification of Seven New Compounds by LC-ESI-MS Journal of Agricultural and Food Chemistry 54, Jan. 11, 2006 (Jan. 11, 2006) pp. 973-979.

Asai et al. Orally Administered Crocetin and Crocins Are Absorbed into Blood Plasma as Crocetin and Its Glucuronide Conjugates in Mice Journal of Agricultural and Food Chemistry 53, Aug. 6, 2005 (Aug. 6, 2005) pp. 7302-7306.

Mariathasan et al., Differential activation of the inflammasome by caspase-1 adaptors ASC and Ipaf Nature 430(8) (2004).

Martinon et al., Gout-associated uric acid crystals activate the NALP3 inflammasome Nature 440(9) (2006).

Volpe et al., Inflammasome as a New Therapeutic Target for Diabetic Complications Recent Patents On Endocrine, Metabolic & Immune Drug Discovery 10, (2016) pp. 56-62.

Choulaki et al., Enhanced activity of NLRP3 inflammasome in peripheral blood cells of patients with active rheumatoid arthritis Arthritis Research & Therapy 17(257) (2015).

Yang et al., NLRP3 inflammasome is essential for the development of chronic obstructive pulmonary disease Int J. Exp Pathol 8(10) Oct. 15, 2015 (Oct. 15, 2015) pp. 13209-13216.

Hutton et al., The NLRP3 inflammasome in kidney disease and autoimmunity Nephrology 21 (2016) pp. 736-744.

Toldo et al., Inhibition of the NLRP3 inflammasome limits the inflammatory injury following myocardial ischemia-reperfusion in the mouse International Journal of Cardiology, 209 (2016) pp. 215-220.

Wang et al., Activation of NLRP3 inflammasome enhances the proliferation and migration of A549 lung cancer cells Oncology Reports 35 (2016) pp. 2053-2064.

Heneka et al., NLRP3 is activated in Alzheimer's disease and contributes to pathology in APP/PS1 mice Nature 493 (7434) Jan. 31, 2013 (Jan. 31, 2013) pp. 674-678.

Baldwin et al., Inhibiting the Inflammasome: A Chemical Perspective Journal of Medical Chemistry, Sep. 30, 2015 (Oct. 30, 2015) p.

Vogelgesang et al. Deposition of Alzheimer's-amyloid is inversely correlated with P-glycoprotein expression in the brains of elderly nondemented humans Pharmacogenetics 12 (2012) pp. 535-541.

Van Asema et al., Blood-brain barrier P-glycoprotein function in Alzheimer's disease Brain 135, Nov. 26, 2011 (Nov. 26, 2011), pp. 181-189.

Cirrito et al., P-glycoprotein deficiency at the blood-brain barrier increases amyloid-β deposition in an Alzheimer disease mouse model The Journal of Clinical Invesigation, 115(11), (2005) pp. 3285-3290.

International Search Report, dated Jan. 1, 2019 for corresponding PCT patent application No. PCT/IN2018/050629.

Written Opinion of the International Search Authority, dated Jan. 1, 2019 for corresponding PCT patent application No. PCT/IN2018/050629.

* cited by examiner

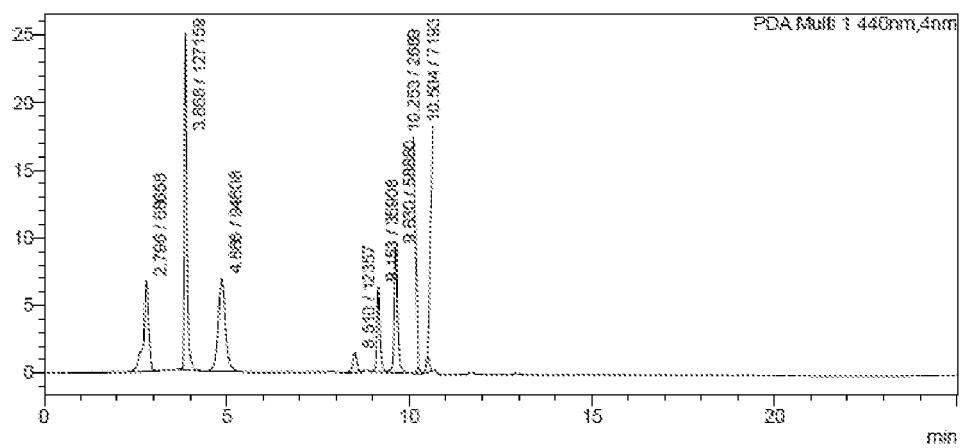
(A)
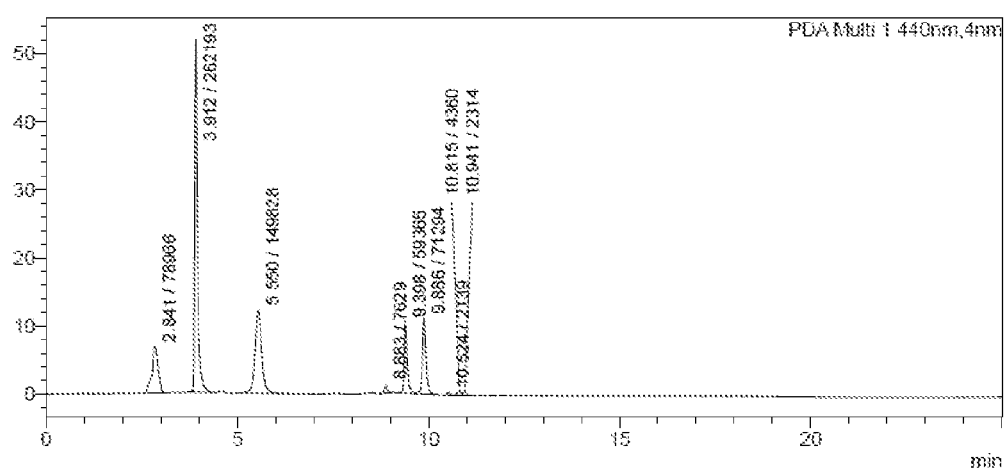
(B)
Figure 1.

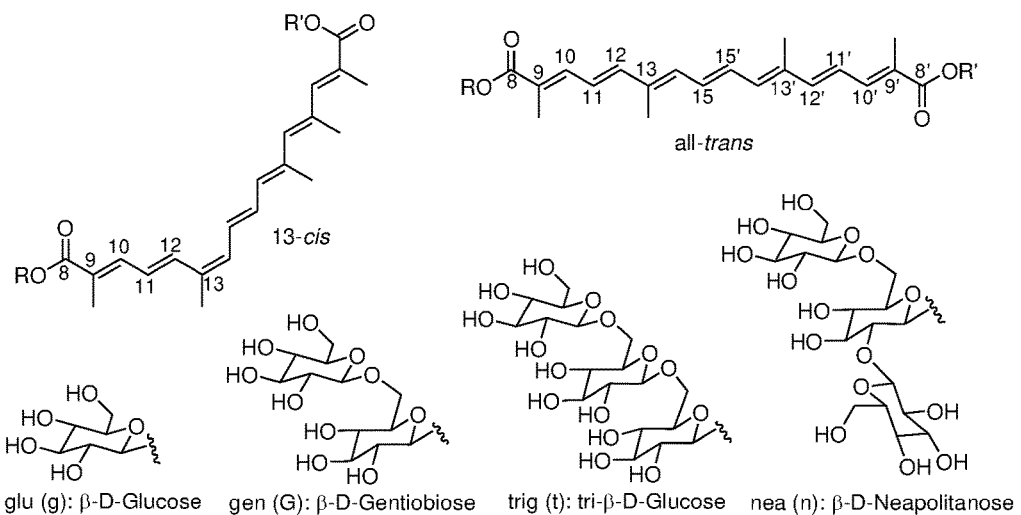

| Crocin/ crocetin | isomer | sugar name (R/R') | no. of glucose | mass |
|---|---|---|---|---|
| trans-5-tG-crocin | trans | trig/gen | 5 | 1138.4 |
| cis-5-tG-crocin | cis | | | |
| trans-5-nG-crocin | trans | nea/gen | | |
| cis-5-nG-crocin | cis | | | |
| trans-4-tG-crocin | trans | nea/glu | 4 | 976.4 |
| cis-4-nG-crocin | cis | | | |
| trans-4-GG-crocin | trans | gen/gen | | |
| cis-4-GG-crocin | cis | | | |
| trans-3-Gg-crocin | trans | gen/glu | 3 | 814.3 |
| cis-3-Gg-crocin | cis | | | |
| trans-2-G-crocin | trans | gen/H | 2 | 652.3 |
| cis-2-G-crocin | cis | | | |
| trans-2-gg-crocin | trans | glu/glu | | |
| cis-2-gg-crocin | cis | | | |
| trans-1-g-crocin | trans | glu/H | 1 | 490.2 |
| cis-1-g-crocin | cis | | | |
| trans-crocetin | trans | H/H | - | 328.2 |
| cis-crocetin | cis | H/H | - | 328.2 |

Figure 2.

SUSTAINED RELEASE FORMULATIONS OF *CROCUS SATIVUS*

RELATED APPLICATIONS

This application is a national phase of International Application No. PCT/IN2018/050629 filed Oct. 4, 2018 and claims priority from Indian Patent Application No. 201711036684 filed Oct. 16, 2017, both incorporated by reference in their entirety.

FIELD OF THE INVENTION

The present invention relates to the formulations for controlled or extended release of certain bioactive compounds, and to the processes for preparation of the same. In particular, the present invention relates to novel sustained release formulations comprising *Crocus sativus* extract or its active ingredient-enriched fraction for the treatment of chronic inflammatory diseases wherein NLRP3 inflammasome is involved.

BACKGROUND OF THE INVENTION

The oral route of administration is typically considered the preferred and most patient-convenient means of drug delivery. With many drugs the basic goal of therapy is to achieve a steady-state blood or tissue level that is therapeutically effective and non-toxic for an extended period of time. Sustained release dosage form is an ideal strategy for the drugs with short half-lives and which require repeated dosing. These dosage forms are designed to release a drug at a predetermined rate in order to maintain a constant drug concentration for a specific period of time with minimum side effects.

*Crocus sativus* L. (Family: Iridaceae), commonly known as saffron or Kesar, is used in Ayurveda and other folk medicines for various purposes, such as an aphrodisiac, antispasmodic and for expectorant effects (Rios J. L. et al., *Phytother. Res.* 1996, 10, 189-193). Modern pharmacological studies have demonstrated that saffron extracts have anti-nociceptive, anti-inflammatory (Hosseinzadeh, H. et al., *BMC Pharmacol.* 2002, 15, 7), antitumor (Escribano J. et al., *Cancer Lett.* 1996, 100, 23), radical scavenger (Abdullaev F. I. et al., *Biofactors,* 1993, 4, 83), anticonvulsant (Hosseinzadeh H. et al., *Arch. Irn. Med.,* 2002, 5, 44), anti-ischemic (Hosseinzadeh H. et al., 2005, *J. Pharm. Pharm. Sci.* 8, 387) and anti-Alzheimer (Abe K. et al., *Brain Res.* 1999, 851, 287; Zhang Y. X. et al. *Biol. Pharm. Bull.* 1994, 17, 217; Khalili M. et al., *Irn. J. Pathol.* 2010, 5, 27; Papandreou M. A. et al., *J. Agric. Food Chem.* 2006, 54, 8762; Khalili M. et al., *Irn. J. Pathol.* 2010, 5, 27) effects. Recently we have shown that, in in-vivo studies *Crocus sativus* extract (50 mg/kg/day, added to mice diet) improves the BBB tightness and function that was associated with reduced Aβ load and related pathological changes in 5XFAD mice. Furthermore, *Crocus sativus* extract upregulated synaptic proteins and reduced neuro-inflammation associated with Aβ pathology in the brains of 5XFAD mice (Batarseh Y. S. et al., *ACS Chem Neurosci.* 2017, 8, 1756-1766).

Saffron contains more than 150 volatile and aroma-yielding compounds along with carotenoids (including zeaxanthin, lycopene, and various α- and β-carotenes). However, saffron's golden yellow-orange color is primarily the result of α-crocin (also called as crocin-1). It is the diester formed from the disaccharide gentiobiose and the dicarboxylic acid crocetin. When crocetin is esterified with two water-soluble gentiobioses, a water-soluble pigment (known as "crocin") is obtained. Crocins are esters formed from the conjugation of various sugars (glucose, gentiobiose, triglucose and neapolitanoside) with dicarboxylic acid of crocetin. Furthermore, geometrically crocetin exists in all-trans and 13-cis forms. Thus, total of 16 crocins are reported, all differing via a type of sugar moiety attached and all-trans or 13-cis geometry (Tarantilis P. A. et al., *J. Chromatogr.* 1995, 699, 107-118; Escribano J. et al., *Cancer Lett.* 1996, 100, 23-30; Pfister S. et al., *J. Agric. Food Chem.* 1996, 44, 2612-2615; *J. Agric. Food Chem.* 2006, 54, 973-979). The chemical structures of crocins are shown in FIG. 2. Among various constituents of saffron, crocin and crocetin are mainly responsible for pharmacological activities. The pharmacokinetic analysis of crocin indicated that it reaches the blood circulation in the hydrolyzed form i.e. as a crocetin. The plasma half-life of crocetin is low (~2 hrs), and it gets eliminated quickly from the blood (Asai A. et al., *J. Agric. Food Chem.* 2005, 53, 7302; Liu T Z and Qian Z Y, *Yao Xue Xue Bao,* 2002, 37, 367). Therefore, development of novel formulations for this botanical drug is essential, which can result in delayed or controlled release of crocin from the formulation in the gastrointestinal tract/intestine. Furthermore, with the great number of therapeutic activities of Saffron extracts, there is a great need to have rigorously standardized extracts of *C. sativus* based on the presence of specific markers, and with a good quality control.

The present invention describes the preparation of standardized botanical extract of *C. sativus* stigma, preparation of crocin-1 enriched fraction, and their novel sustained release formulations for delayed or modified release of crocin-1 (an active ingredient) and inhibitory activity against NLRP3 inflammasome. The preclinical characterization of standardized botanical extract of *C. sativus* stigma has been published (Bharate S S et al., *ACS Omega* 2018, 3, 9572-9585).

Inflammasomes are high molecular weight complexes that sense and react to injury and infection. The inflammasome is responsible for activation of inflammatory processes (Mariathasan S. et al., *Nature* 2004, 430, 213), and has been shown to induce cell pyroptosis, a process of programmed cell death distinct from apoptosis. Their activation induces caspase-1 activation and release of interleukin-1β, a pro-inflammatory cytokine involved in both acute and chronic inflammatory responses. There is increasing evidence that inflammasomes, particularly the NLRP3 inflammasome, act as guardians against noninfectious material. Inappropriate activation of the NLRP3 inflammasome contributes to the progression of many non-communicable diseases such as gout (Martinon F. et al, *Nature* 2006, 440, 237), type-II diabetes (Caroline M O et al., *Recent Pat Endocr Metab Immune Drug Discov.* 2016, 10, 56-62), rheumatoid arthritis (Choulaki C. et al., *Arthritis Res Ther.* 2015, 17, 257), chronic obstructive pulmonary diseases (Yang W. et al., *Int J ClinExpPathol.* 2015, 8, 13209), kidney diseases (Hutton H L et al., *Nephrology* 2016, 21, 736), myocardial ischemia (Toldo S. et al., *Int J Cardiol.* 2016, 209, 215), cancer (Wang Y. et al, *Oncol Rep.* 2016, 35, 2053-2064) and Alzheimer's disease (Heneka, M. T. et al. *Nature* 2012, 493, 674-678). Therefore, inhibiting the NLRP3 inflammasome may significantly reduce damaging inflammation and is therefore regarded as a therapeutic target for these chronic inflammatory diseases (Baldwin A. G. et al., *J. Med. Chem.* 2016, 59, 1691-710).

Normally, amyloid-beta load in the brain is low due to clearance by the BBB transporter pumps like P-gp and LRP-1 but with the aging, this clearance mechanism is compromised, consequently fine balance between amyloid-beta production and its clearance from brain get disturbed which ultimately leads to accumulation of large amount of amyloid-beta in brain resulting in neurotoxicity (Vogelgesang, S. et al., *Pharmacogenetics* 2002, 12, 535-541; Assema V. et al., 2012, *Brain*, 135, 181-189). As the amyloid-beta load in brain is cleared either by metabolism or efflux from BBB transporter pumps like P-gp and low-density lipoprotein receptor-related protein 1 (LRP1) (Cirrito, J. R., et al., *J. Clin. Invest.* 2005, 115, 3285-3290); therefore detoxication of amyloid-beta by increasing the P-gp and LRP1 mediated amyloid-beta efflux function could be a novel way of protecting brain from amyloid-beta toxicity.

OBJECTIVES OF THE INVENTION

The objective of this invention to provide novel sustained release formulations of standardized extract of *Crocus sativus*.

It is also an objective of this invention to provide novel sustained release formulations containing elevated concentrations of at least one of specific markers obtained by means of the process.

It is another objective of this invention to provide the use and method of application of this formulation for treatment of chronic inflammatory diseases wherein NLRP3 inflammasome is involved.

SUMMARY OF THE INVENTION

The present invention seeks to provide novel and improved sustained release oral formulations of *Crocus sativus* for supplying optimum plasma concentrations of the biologically active compounds contained in the plant such as "crocins". There is thus provided in accordance with a preferred embodiment of the invention an orally-administrable formulation for the controlled release of "crocin-1".

In one preferred embodiment of the invention, the orally-administrable formulation for the controlled release of active ingredient 'crocin-1' comprises granulated hydroalcoholic extract or crocin-enriched fraction and at least one carrier, adjuvant or excipient thereof, and is characterized in that the total in vitro dissolution time of the formulation required for release of 75% of the active ingredient available from the formulation, is between about 4 and about 18 hours, as determined by the U.S.P. basket method at a speed of 50 rpm, and temperature of 37° C.±0.5, using 900 ml of dissolution media.

In one preferred embodiment of the invention, said formulation contains weight ratio of hydroalcoholic extract/fraction of *Crocus sativus*: polymer(s) is in the range of 30:70 to 70:30.

In another preferred embodiment of the invention, the formulation is characterized in that it contains from 20 to 80% w/w hydroalcoholic extract or crocin-1 enriched fraction.

In another preferred embodiment of the invention, the formulation is in the form selected from the group consisting of a matrix tablet or a hard gelatin two-piece capsule filled with polymeric granules or microparticles of granulated extract.

In another preferred embodiment of the invention, the formulation comprises granulated extracts mixed or coated with an excipients or polymers selected from the group consisting of hydroxypropyl methylcellulose K4M (HPMC-K4M), hydroxypropyl methylcellulose K15M (HPMC-K15M), ethyl cellulose 10-100 cps, hydroxy propyl methyl cellulose phthalate (HPMCP), hydroxy propyl methyl phthalate cellulose acetate succinate (HPMPCAS), cellulose acetate phthalate (CAP), eudragit S100, eudragit L100, eudragit RS 100, eudragitRL 100, polyethylene oxide, xanthan gum, chitosan, gelatin, sodium alginate, magnesium stearate, silicon dioxide, dicalcium phosphate, microcrystalline cellulose, lactose, starch and talc.

In another preferred embodiment of the invention, the binder is selected from group consisting of polyvinylpyrrolidone K30 and polyvinylpyrrolidone K15 and binder solution is prepared by 5-10% w/v in isopropyl alcohol, methanol, ethanol or propanol.

In another preferred embodiment of the invention, said extract contains at least 15% w/w of active ingredient trans-crocetin-di-($\beta$-D-gentiobiosyl)ester (crocin-1).

In another preferred embodiment of the invention, said fraction contains at least 30% w/w of active ingredient trans-crocetin-di-($\beta$-D-gentiobiosyl)ester (crocin-1).

The invention also comprises a process for the preparation of an orally-administrable formulation for the controlled release of a granulated extract. The steps for preparation of said formulation comprising granulated extract and at least one carrier, comprises:

a) extraction of dried stigmas of *C. sativus* with ethanol: water (1:1) to yield an extract solution;

b) concentrating the extract solution first by vacuum drying followed by freeze drying to yield dry powder of hydroalcoholic extract. The extractive value of hydroalcoholic extract on dry weight basis is found to be 45-55% w/w of the dry botanical raw material.

c) partitioning the hydroalcoholic extract between water and ethyl acetate.

d) concentrating the water layer as obtained in step 'c' first by vacuum drying followed by freeze drying to yield dry powder of crocin-enriched fraction (IIIM-141-CEF). The extractive value of crocin-enriched fraction on dry weight basis is found to be 45-50% w/w of the IIIM-141-A002 extract and 25-30% w/w of the dry botanical raw material.

e) Mixing the hydro alcoholic extract or crocin-enriched fraction with excipient(s) in mortar and pestle, following by addition of 10% PVP-K30 solution in isopropanol (as a binder) to form a dough.

f) Passing the obtained dough through sieve #10 to get polymeric granules of hydro alcoholic extract or crocin-enriched fraction.

g) Drying of obtained granules in vacuum desiccator at room temperature, followed by filling in two-piece empty hard gelatin capsules.

h) wherein said formulation is characterized in that the total in vitro dissolution time of said formulation required for release of 75% of the active ingredients from said formulation is between about 4 and about 18 hours, as determined by to the U.S.P. basket method at a speed of 50 rpm, and temperature of 37° C.±0.5, using 900 ml of dissolution media.

In another aspect of the present invention, said formulation comprises extract of *Crocus sativus* in an amount of 30-70% by weight of the formulation and at least 4.5% of active ingredient trans-crocetin di-($\beta$-D-gentiobiosyl)ester (crocin-1).

In another aspect of the present invention, in the comparative pharmacokinetic study conducted in SD rats, the sustained release formulation (IIIM-141-SR) displayed 3.3-fold enhancement in the AUC of the crocetin (a bioactive metabolite, formed via enzymatic hydrolysis in the plasma/GIT) in comparison to the plain extract.

In another aspect of the present invention, the ratio of crocin:crocetin in the plasma of rats was enhanced from 1:4 to 1:9 in SR formulation (IIIM-141-SR).

In another aspect of the present invention, the prolonged release of the bioactive constituent (a hydrolyzed metabolite crocetin) was observed up to 24 hrs in the rat plasma in SR formulation (IIIM-141-SR) in comparison to the plain extract.

In another aspect of the present invention, a method for enrichment of one of the active constituent is provided.

In one more embodiment of the invention, the standardization of the C. sativus extract is provided to identify and quantify amount of specified marker in the standardized extract of C. sativus by HPLC.

In another embodiment of the invention, standardized extract of C. sativus (IIIM-141-A002) displayed significant inhibition of NLRP3 inflammasome in human monocytic THP-1 cells.

In one particular aspect of the present invention, an extract of C. sativus is provided, which comprises active components for NLRP3 inhibition, and related manifestations and disorders with a pharmaceutically acceptable carrier, and methods of using the same. Accordingly, the present invention is directed generally to the sustained release formulations of standardized extracts or crocin-1 enriched fraction of C. sativus for treatment of chronic inflammatory diseases wherein NLRP3 inflammasome is involved.

In another aspect of the invention, chronic inflammatory diseases comprises gout, type II diabetes, rheumatoid arthritis, chronic obstructive pulmonary diseases, kidney diseases, myocardial ischemia, cancer and Alzheimer's disease.

In one more embodiment of the invention, standardized extract of C. sativus display significant increase in P-gp efflux function (as determined by Rh123) and increase in P-gp protein expression in P-gp endogenously expressing adenocarcinoma cells (LS-180 cells) in-vitro.

BRIEF DESCRIPTION OF THE DRAWINGS

FIG. 1 shows the HPLC chromatograms of hydroalcoholic extract of Crocus sativus stigma (A) and crocin-1 enriched fraction (B). Labels of each peak indicate the retention time and area under the curve. Both HPLC chromatograms are recorded at 50 µg/ml concentration. The marker component crocin-1 is appearing at $t_R$=3.86 min.

FIG. 2 shows chemical structures of crocins present in Crocus sativus. In literature, varying nomenclature has been given to different crocins; therefore for better clarity we have shown the name of isomer followed by number of sugars it contain and name of sugars for each crocin. e.g. "trans-5-tG-crocin" is the trans-crocetin ester comprising tri-β-D-glucoside (t) and β-D-gentiobioside (G) sugars.

ABBREVIATIONS

Figure 3:
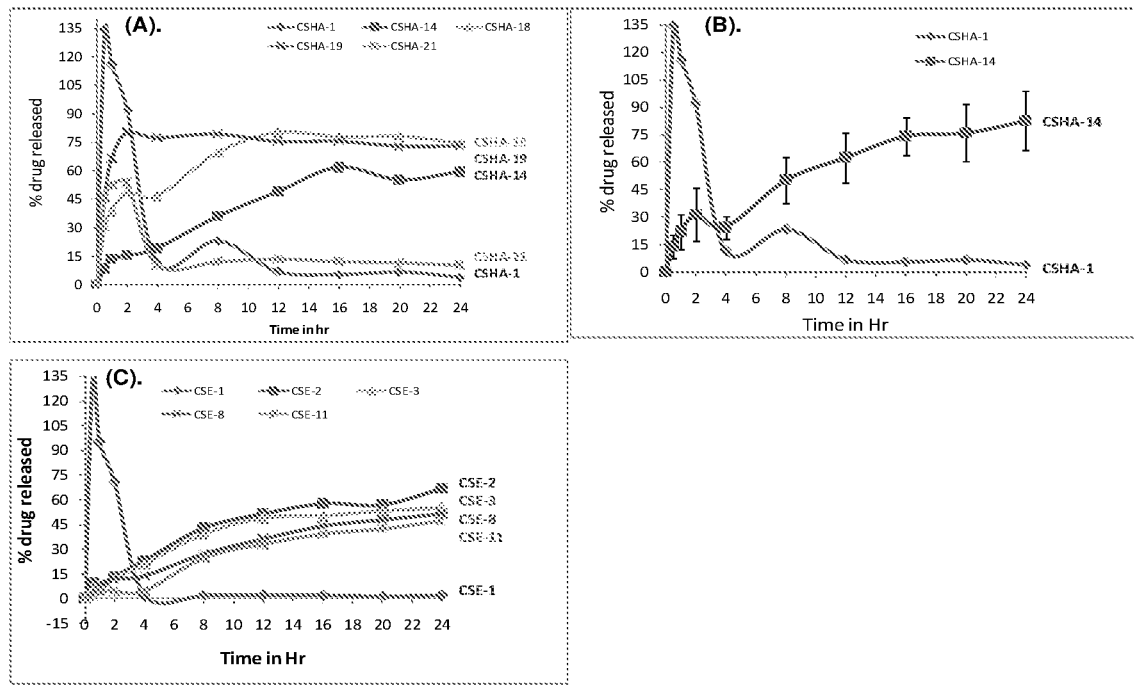
FIG. 3 shows the in-vitro dissolution profiles of developed sustained release formulations. (A). In-vitro dissolution profile of hydroalcoholic extract (CSHA-1) and its sustained release formulations CSHA-14, CSHA-18, CSHA-19 and CSHA-21; (B). In-vitro dissolution profile of sustained release formulations CSHA-14 (in triplicate); (C). In-vitro dissolution profile of crocin-1 enriched fraction (CSE-1) and its sustained release formulations CSE-2, CSE-3, CSE-8 and CSE-11. In this study, the % release of crocin-1 was determined by HPLC analysis.

AUC, area under the curve; aCSF, artificial cerebrospinal fluid; CAP, cellulose acetate phthalate; HBSS, Hank's buffered salt solution; HPMCP, hydroxy propyl methyl cellulose phthalate; HPMC-K15M, hydroxypropyl methyl cellulose-K15M; LS-180 is a colon adenocarcinoma cell line; LRP1, low-density lipoprotein receptor-related protein 1; NLRP3, NOD-like receptor (NLR) subfamily; PVP-K30, polyvinylpyrrolidone K 30; P-gp, p-glycoprotein; Rh123, rhodamine 123; SAM, Swiss Albino mice; STZ, streptozotocin; THP-1 is a human monocytic cell line; TBST is mixture of tris-buffered saline (TBS) and Tween 20; SD rat, Sprague Dawley rat.

DETAILED DESCRIPTION OF THE INVENTION

The present invention provides novel sustained release formulations of hydroalcoholic extract and crocin-1 enriched fraction of Crocus sativus stigma for treatment of chronic inflammatory diseases involving NLRP3 inflammasome. More specifically, this invention is further directed to methods of preparation of hydroalcoholic extract or active ingredient enriched fraction from the dried stigmas of Crocus sativus using ethanol and water in ratio of 1:1. The hydroalcoholic extract (IIIM-141-A002) and crocin-enriched fraction (IIIM-141-CEF) are standardized for the content of major active constituent "crocin-1". The hydroalcoholic extract and crocin-enriched fraction contain 33.12±3.26% and 55.19±1.82% of crocin-1, as determined by HPLC analysis.

Particularly, this invention provides the method for preparation of novel sustained release formulations wherein the extract is wet-granulated using excipients, biodegradable polymers and/or non-biodegradable polymers alone or in combination, and the said granules are either filled into a capsule or compressed into a tablet. The said formulation comprising a granulated extract of Crocus sativus with polymers results in sustained release of the extract in the gastrointestinal tract.

Moreover, this invention provides formulations wherein the total in-vitro dissolution time of said formulations required for release of 60-80% of the active ingredient "crocin-1" is between 8 to 16 hours, as determined by the U.S.P. dissolution apparatus by basket method at a speed of 50 rpm, and temperature of 37° C.±0.5, using 900 ml of dissolution media. The sustained release of the bioactive constituent was observed in the rat pharmacokinetic study;

which validated the in-vitro dissolution results. After oral administration of crocin-enriched fraction (IIIM-141-CEF) as well as IIIM-141-SR formulation in rats, it was observed that crocin, the major constituent of *Crocus sativus* extract, gets metabolized to "crocetin", which is the bioactive metabolite. The crocin-enriched fraction (IIIM-141-CEF) and its SR formulation, when administered orally at equivalent dose (a dose equivalent to 45 mg/kg of crocin), the significantly higher AUC for "crocetin" was observed in case of SR formulation in comparison to the plain extract. This result indicated that SR formulation controls the release of extract, leading to the release of bioactive constituent for prolonged time. As an overall effect of this, the higher amount of crocetin is available in the blood circulation, which ultimately results in improved therapeutic effect.

Figure 5:
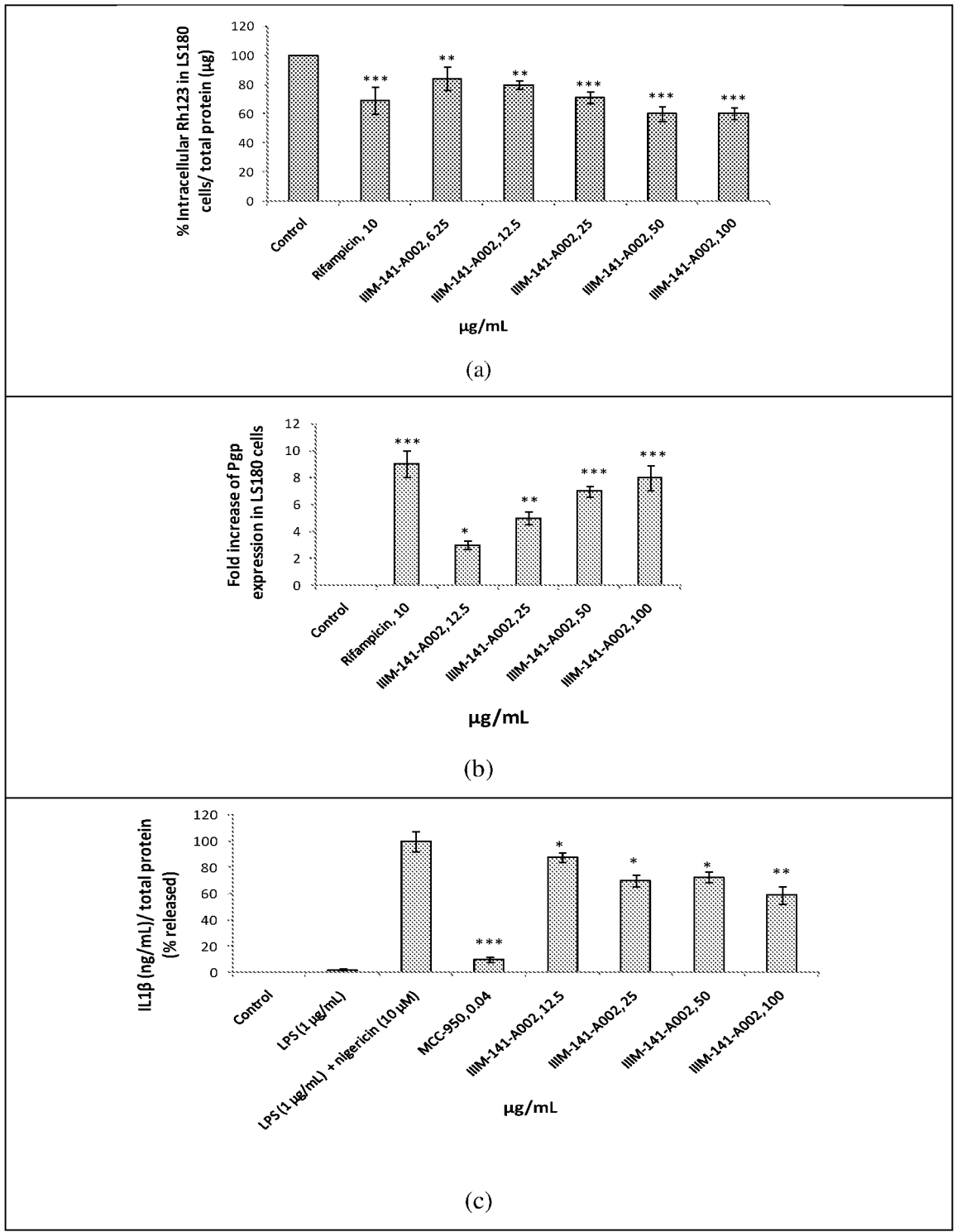
FIG. 5 P-gp induction activity and NLRP3 inflammasome inhibition activity of IIIM-141-A002 (a) the % intracellular Rh123 levels at various concentrations of IIIM-141-A002 extract in LS-180 cells; (b) effect of IIIM-141-A002 on P-gp expression in LS-180 cells; (c) inhibition of NLRP3 inflammasome by IIIM-141-A002 in human monocytic THP-1 cells FIG. 6 Effect of IIIM-141-A002 on memory and learning in behavioral models (a) effect of IIIM-141-A002 on streptozotacin (STZ) induced memory deficit in Morris Water Maze test in SD rats; (b) effect of IIIM-141-A002 on scopolamine induced memory deficit in passive avoidance test in Swiss albino mice.

The significant inhibition of NLRP3 inflammasome in human monocytic THP-1 cells by IIIM-141-A002 is depicted in FIG. 5. The nigericin induced release of IL-1beta was significantly suppressed by hydroalcoholic extract (IIIM-141-A002) at the test concentration of 25 µg/ml. The effect was further enhanced in a concentration dependent manner from 25 to 100 µg/ml.

The spectrums of conditions for which the inventive extract can be used for inflammatory conditions where NLRP3 inflammasome is involved, includes, but not limited to gout, type II diabetes, rheumatoid arthritis, chronic obstructive pulmonary diseases, kidney diseases, myocardial ischemia, cancer, Alzheimer's disease.

The following examples, which include preferred embodiments, will serve to illustrate the practice of this invention, it being understood that the particulars shown are by way of example and for purpose of illustrative discussion of preferred embodiments of the invention Following examples are given by way of illustration and should not construe to limit the scope of invention.

EXAMPLE 1

Preparation of Hydroalcoholic Extract (IIIM-141-A002) and Crocin-Enriched Fraction (IIIM-141-CEF)

The authentic plant material of *Crocus sativus* (stigma) was purchased from local market of Srinagar (Jammu and Kashmir State, India). The plant material was taxonomically characterized, and a voucher specimen was deposited in the Janaki Animal Herbarium at the CSIR-IIIM, Jammu. Dried-material was extracted with water: ethanol (1:1) mixture and then freeze dried.

The steps include:
1. Mixing the ground plant drug (100 g) with an extracting hydro-alcoholic solution in the proportion of 1:1 or 2:1 (water: alcohol), using ethanol or methanol as alcohol, in the initial proportion of 1 part plant ingredient (in grams) to 10 parts of hydro-alcoholic solution (in ml), based on the mass of the materials. Performing the extraction of the compounds for a period of 3-6 hours at 20-30° C. in a closed reactor. Filtering the mixture yields a first intermediary hydro-alcoholic extract and a first residue consisting of the components of the non-extracted plant drug.
2. Mixing the first residue consisting of the components of the non-extracted plant drug with a fresh extracting hydro-alcoholic solution, constituted of a mixture of ethanol and water in the proportion 1:1. Filtering the mixture yields a second intermediary hydro-alcoholic extract and a second residue constituted of the components of the non-extracted plant drug;
3. Mixing the second residue consisting of the components of the non-extracted plant drug with a fresh extracting hydro-alcoholic solution, constituted of a mixture of ethanol and water in the proportion 1:1. Filtering the mixture yields a third intermediary hydro-alcoholic extract and a third residue constituted of the components of the non-extracted plant drug;
4. All three hydro-alcoholic extracts were combined and ethanol is evaporated from the mixture by vacuum assisted evaporation (temperature of 40° C., vacuum of 250 mm/Hg) until the mass corresponds to approximately 50% of the mass of the mixture obtained. Concentrated mass is further dried using lyophilization to generate dry powder extract (45.2 g—IIIM-141-A002). The extractive value of hydroalcoholic extract on dry weight basis was found to be 45-55% w/w of the dry botanical raw material.

The active ingredient [trans-crocetin di-(β-D-gentiobiosyl) ester] (crocin-1) enriched extract was prepared using following procedure:
1. The hydroalcoholic extract (IIIM-141-A002) as obtained above, was partitioned between water and ethyl acetate.
2. The water portion was concentrated over vacuo rotavapor to get dried powder of active ingredient [trans-crocetin di-(β-D-gentiobiosyl)ester] enriched extract (IIIM-141-CEF). The extractive value of crocin-1 enriched fraction (from dried plant material) on dry weight basis was found to be 45-50% w/w of the IIIM-141-A002 extract and 25-30% w/w of the dry botanical raw material.

The hydroalcoholic extract is primarily a mixture of crocins, which are crocetin glycosides. The HPLC/LCMS analysis indicated that amongst the total 16 crocetin-esters (crocins) reported (chemical structures are shown in FIG. 2), trans-4-GG-crocin is the major crocetin-ester. The HPLC chromatogram (FIG. 1A) showed presence of primarily six crocins including trans-5-ng-crocin ($t_R$=2.8 min), trans-4-GG-crocin ($t_R$=3.8 min)trans-3-Gg-crocin ($t_R$=5.0 min), trans-2-gg-crocin ($t_R$=8.8 min), cis-4-GG-crocin ($t_R$=9.7 min) and cis-3-Gg-crocin ($t_R$=10.6 min) The trans-4-GG-crocin being the major crocin, it was isolated and characterized. The % content of trans-4-GG-crocin in hydroalcoholic extract (IIIM-141-A002) and crocin-1 enriched fraction (IIIM-141-CEF) was determined using HPLC analysis.

HPLC analysis was performed on the Shimadzu HPLC system connected to a PDA detector, and C8 (Intersil, 25 cm×4.6 mm, 5µ) column. Mobile phase consisted of acetonitrile (A) and 0.1% formic acid in water (B). The gradient system comprised of 70% B (0.01 min), 70% B (2 min), 30% B (7 min), 30% B (15 min), 70% B (20 min), 70% B (25 min) at a flow rate of 1 ml/min.

The hydroalcoholic extract was found to contain 33.11±3.25 (average of six different experiments) of trans-4-GG-crocin. Thus, the % content of trans-4-GG-crocin in *Crocus sativus* (stigma) dried material was found to be 15.6%. The trans-4-GG-crocin enriched fraction (IIIM-141-CEF) was found to contain 55.19±1.82% of trans-4-GG-crocin. The chemical structures of all crocins are provided in FIG. 2.

EXAMPLE 2

Preparation of Novel Sustained Release Formulations

The hydroalcoholic extract (IIIM-141-A002) or crocin-1 enriched fraction (IIIM-141-CEF) and excipient(s) were weighed accurately and mixed thoroughly using mortor and pestle. This mixture was kneaded using 10% PVP-K30 solution in isopropanol (as a binder) to form a dough. This dough was then passed through sieve #10. The obtained granules were dried in vacuum dessicator at room temperature. The formulations were assayed for crocin-1 content using HPLC method as mentioned in example 1. Based on the results of assay, formulation equivalent to 50 mg of crocin-1 was filled into the hard gelatin capsules of size '0'. These capsules were analyzed for in-vitro dissolution profile.

Some of the composition of sustained release formulations are provided in Table 1.

filled with plain hydroalcoholic extract (CSHA-1) as well as in crocin-1 enriched fraction (CSE-1). However, capsules filled with novel sustained release formulations CSHA-14, CSHA-18, CSHA-19, CSE-2, CSE-3, CSE-8 and CSE-11 resulted in a delayed release of crocin-1 with 60-75% release up to 24 hrs.

The dissolution profiles of formulations of hydroalcoholic extract of *Crocus sativus* are shown in FIG. 3A. From these formulations, the best formulation CSHA-14 was studied for dissolution profile in triplicate, and the release profile is

TABLE 1

Composition of each formulation and % release of crocin-1 after time intervals during dissolution study

| Sr No | Formulation | Composition[a] | % release of crocin-1 after | | |
|---|---|---|---|---|---|
| | | | 0.5 h | 12 h | 24 h |
| 1 | CSHA-14 | IIIM-141-A002: 2 g<br>HPMC-K15M: 1.333 g | 8.5 | 62 | 83 |
| 2 | CSHA-18 | IIIM-141-A002: 2 g<br>HPMC-K15M: 0.888 g<br>Ethyl cellulose 10 cps: 0.444 g | 31 | 80 | 74 |
| 3 | CSHA-19 | IIIM-141-A002: 2 g<br>HPMC-K15M: 0.999 g<br>Ethyl cellulose 10 cps: 0.333 g | 46 | 75 | 73 |
| 4 | CSHA-21 | IIIM-141-A002: 2 g<br>HPMC-K15M: 0.666 g<br>Ethyl cellulose 10 cps: 0.666 g | 46 | No further release after 2 hrs (too much retardation in drug release) | |
| 5 | CSE-2 | IIIM-141-CEF: 1 g<br>HPMC-K4M: 0.7 g | 5 | 52 | 67 |
| 6 | CSE-3 | IIIM-141-CEF: 1 g<br>HPMC-K15M: 0.7 g | 9.6 | 49 | 55 |
| 7 | CSE-8 | IIIM-141-CEF: 1 g<br>HPMC-K4M: 0.8 g<br>Eudragit RS100: 0.2 g | 8.2 | 36 | 51 |
| 8 | CSE-11 | IIIM-141-CEF: 1 g<br>HPMC-K15M: 0.8 g<br>Eudragit RS100: 0.2 g | 4.6 | 33 | 47 |
| 9 | CSHA-1 (plain hydroalcoholic extract filled in capsules) | IIIM-141-A002: 1 g | 100 | 0 | 0 |
| 10 | CSE-1 (plain crocin-1 enriched fraction filled in capsules) | IIIM-141-CEF: 1 g | 100 | 0 | 0 |

[a]A 10% PVP-K30 solution in isopropanol was added as a binder in each formulation to form a dough.

EXAMPLE 3

Dissolution Profile of Sustained Release Formulations

The dissolution profile of plain hydroalcoholic extractor crocin-1 enriched fraction and their sustained release formulations was studied using USP dissolution apparatus as per the protocol given in USP 2011 (The United States Pharmacopoeial Convention. 2011, Pages 1-8). Lab-India Dissolution Tester (Model: DS 8000; apparatus 1—Basket Apparatus) was used for this study. Various parameters are: RPM=50; Temp.=37° C.±0.5; Volume of dissolution medium=900 ml; Dissolution medium=(A) Hydrochloric acid buffer (pH 1.2) for first 2 h, (B) Phosphate buffer pH 6.8; Sampling time points (h)=0.5, 1, 2, 4, 8, 12, 16, 20 and 24.

The percent release of trans-crocetin di-(β-D-gentiobiosyl) ester ("crocin-1") from developed formulations was determined by HPLC analysis (FIG. 1). Results showed that crocin-1 gets 100% released in 30 min in case of capsules shown in FIG. 3B. Thus, the CSHA-14 was considered as the optimum batch with sustained release profile over a period of 24 h. Similarly, amongst various combination of polymer to IIIM-141-CEF attempted, the best four formulations CSE-2, CSE-3, CSE-8 and CSE-11 resulted in a delayed release of crocin-1 with 45-70% release up to 24 hrs (FIG. 3C). The % release of crocin-1 after 0.5 and 24 hrs. is tabulated in Table 1.

The summarized overview of best formulations with their $T_{10\%}$, $T_{50\%}$ and $T_{75\%}$ values are shown in Table 2. The release half-life ($T_{50\%}$) for crocin-1 in plain extract and fraction is <0.5 hr, whereas it is 8 and 12 hrs. in novel sustained release formulations CSHA-14 and CSE-2. The $T_{75\%}$ (time taken to release 75% of drug from the formulation) for crocin-1 in plain extract and fraction is <0.5 hr, whereas it is 20 and 24 hrs. in novel sustained release formulations CSHA-14 and CSE-2. This is indicative of the delayed release of crocin-1 from novel formulations.

TABLE 2

Dissolution release profile of crocin-1 in optimized formulations of Crocus sativus

| Formulation | Batch no. | $t_{10\%}$ (hr) | $t_{50\%}$ (hr) | $t_{75\%}$ (hr) |
|---|---|---|---|---|
| Formulations of hydroalcoholic extract | CSHA-1 (plain hydroalcoholic extract) | — | — | <0.5 |
| | CSHA-14 | ~0.5 | 8.0 | 20.0 |
| Formulations of crocin-enriched fraction | CSE-1 (plain crocin-enriched fraction) | — | — | <0.5 |
| | CSE-2 | ~0.5 | 12.0 | ~24.0 |

$t_{10\%}$ = time taken to release 10% of drug from the formulation; $t_{50\%}$ = dissolution half-life; $t_{75\%}$ = time taken to release 75% of drug from the formulation.

EXAMPLE 4

Pharmacokinetic Study of IIIM-141-A002 Extract and its SR Formulation in SD Rats For comparative oral pharmacokinetic study of plain extract (IIIM-141-A002) and SR formulation (filled in 9 el capsules), the dose equivalent to 45 mg/kg of crocin was administered in SD rats in both these groups. Blood samples were collected (n=3/time point) at 0.083 (IV only), 0.25, 0.5, 1, 2, 4, 8 and 24 h, post-dose. At each time point about 200 µL of blood was collected by jugular vein into a labeled microfuge tube containing 200 mM K2EDTA solution (20 µL per mL of blood) and equivalent volume of heparinized saline was replaced following sample collection. The blood samples were processed to obtain the plasma samples within 30 min of scheduled sampling time. All plasma samples were stored below −60° C. until bioanalysis. The plasma samples were analyzed for crocin and crocetin content using a fit-for purpose LC-MS/MS method with a lower limit of quantification (LLOQ) of 9.95 ng/mL. The pharmacokinetic parameters of crocin and crocetin were calculated using the non-compartmental analysis tool of validated Phoenix® WinNonlin® software (version 6.3).

Figure 4:
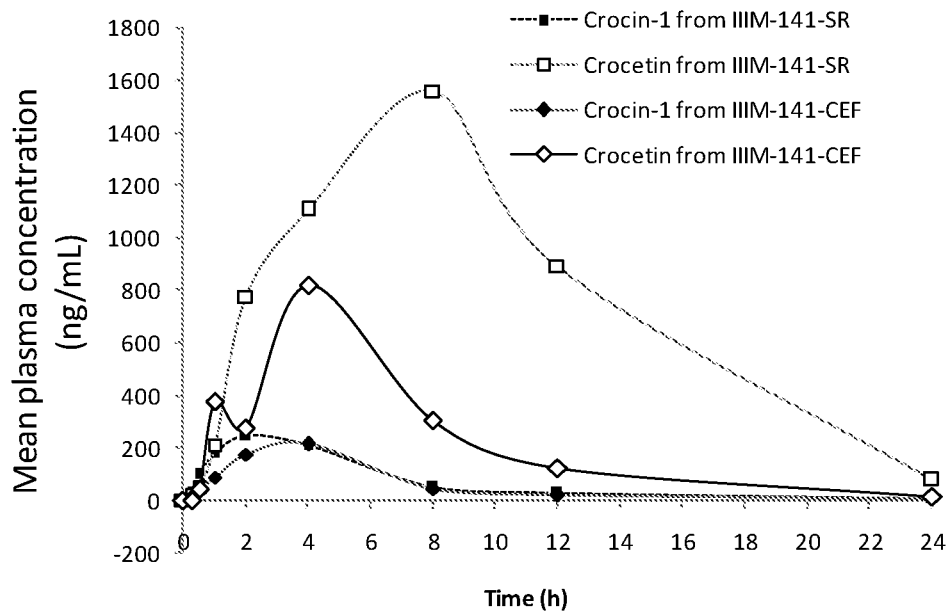
FIG. 4 Comparative oral pharmacokinetic study of plain extract (IIIM-141-CEF) and SR formulation (IIIM-141-SR) in SD rats (route of administration: PO; dose equivalent to 45 mg/kg of crocin-1).

The PK parameters of crocin-1 and crocetin after administration of crocin-1 enriched fraction (IIIM-141-CEF) and its sustained release formulation (IIIM-141-SR) at a dose equivalent to 45 mg/kg of crocin-1 in SD rats are shown in Table 3. The time-plasma concentration curve of extract and formulation is depicted in FIG. 4. The PK results indicate that when the crocin-1 enriched fraction is administered in rats, the majority of crocin-1 gets metabolized to crocetin. The $AUC_{inf}$ of crocin-1 and crocetin after administration of crocin-1 enriched fraction (IIIM-141-CEF) were found to be 1360 and 5540 µg·h/mL, respectively (the ratio of crocin-1 to crocetin in plasma is 1:4). When the equivalent dose of the extract IIIM-141-CEF was administered in the form of SR formulation, the crocetin concentration in plasma was increased by 3.3 fold. The $AUC_{inf}$ of crocetin was changed from 5540 to 18300 µg~h/mL Similarly, the $C_{max}$ was also increased by 1.79 fold. Interestingly, the ratio of crocin-1 to crocetin in plasma was also increased, from 1:4 to 1:9, indicating that more amount of crocetin (which is a bioactive constituent) is available in the blood circulation to display therapeutic effect at the site of action.

Table 3. PK parameters of crocin-1 and crocetin after administration of crocin-1 enriched fraction (IIIM-141-CEF) and its sustained release formulation (IIIM-141-SR) at a dose equivalent to 45 mg/kg of crocin-1 in SD rats.

TABLE 3

PK parameters of crocin-1 and crocetin after administration of crocin-1 enriched fraction (IIIM-141-CEF) and its sustained release formulation (IIIM-141-SR) at a dose equivalent to 45 mg/kg of crocin-1 in SD rats.

| Parameters | IIIM-141-CEF (dose equivalent to 45 mg/kg of crocin-1) | | IIIM-141-SR (dose equivalent to 45 mg/kg of crocin-1) | | Fold-change (between IIIM-141-CEF and IIIM-141-SR) | |
|---|---|---|---|---|---|---|
| | Crocin-1 | Crocetin | Crocin-1 | Crocetin | Crocin-1 | Crocetin |
| $T_{max}$(h) | 4 | 4 | 2 | 8 | 0.5 | 2 |
| $C_{max}$ (µg/mL) | 213 | 861 | 253 | 1540 | 1.18 | 1.79 |
| $AUC_{last}$(µg · h/mL) | 1340 | 5460 | 1520 | 17900 | 1.13 | 3.28 |
| $AUC_{inf}$(µg · h/mL) | 1360 | 5540 | 1970 | 18300 | 1.44 | 3.30 |
| $T_{1/2}$ (h) | 4.54 | 3.53 | 5.60 | 4.28 | 1.23 | 1.21 |
| $T_{last}$(h) | 24 | 24 | 24 | 24 | 1 | 1 |
| Ratio of crocin-1: crocetin(based on $AUC_{inf}$) | 1:4 | | 1:9 | | Changed from 1:4 to 1:9 | |

EXAMPLE 5

P-gp Induction Activity of IIIM-141-A002 in LS-180 Cells

IIIM-141-A002 was screened for its ability to induce P-gp using rhodamine 123 (Rh123) cell exclusion method. In this method, P-gp function was evaluated in terms of rhodamine 123 (Rh123) accumulations and efflux. Briefly, the protocol used is as follows: Colorectal LS-180 cells [obtained from ECACC (European Collection of Cell Cultures) catalogue number: 87021202; passage number 52] were seeded at a density of $2 \times 10^4$ per well of 96 well plate and were allowed to grow for next 24 h. Cells were further incubated with the test samples, and were diluted to the final desired series of concentrations and rifampicin (standard) to a final concentration of 10 µM in complete media for 48 h. The final concentration of DMSO was kept at 0.1%. Test sample and standard rifampicin were removed and cells were incubated with HBSS solution for 40 minutes before further incubation with HBSS solution (containing 10 µM of Rh123 as a P-gp substrate) for 90 minutes. At the end of Rh123 treatment cells were washed four times with cold PBS followed by cell lysis for 1 h by using 200 µl of lysis buffer (0.1% Triton X-100 and 0.2 N NaOH). A total of 100 µl of lysate was used for reading fluorescence of Rh123 at 485 nm/529 nm Samples were normalized by dividing fluorescence of each sample with total protein present in the lysate.

IIIM-141-A002 treatment in LS-180 colon cancer cells at various concentrations ranging from 6.25 µg/ml to 100 µg/ml led to significant increase in the efflux of substrate rhodamine 123 dye as determined by decrease (by 16-40%) in intracellular % Rh123 levels (FIG. 5a). Rifampicin was used as a positive control in this study. Rifampicin at 10 µg/mL showed decrease in intracellular accumulation of Rh123 levels (by 31%) in LS180 cells, in comparison with control (100%).

EXAMPLE 6

Western Blot Analysis of IIIM-141-A002 in LS-180 Cells

The protein lysates were prepared and total protein content in lysate were measured employing Bio-Rad protein assay kit using bovine serum albumin as standard. Proteins aliquots (70 µg) were resolved on SDS-PAGE and then electro transferred to PVDF membrane overnight at 4° C. at 30V. Non-specific binding was blocked by incubation with 5% non-fat milk in Tris-buffered saline containing 0.1% Tween-20 (TBST) for 1 h at room temperature. The blots were probed with P-gp antibody for 4 h and washed three times with TBST. Blot was then incubated with horseradish peroxidase conjugated anti-mouse secondary antibody for 1 h, washed again three times with TBST and signals detected using ECL plus chemiluminescence's kit on BioRadChemi-Doc XRS system.

Western-blot results clearly indicate that IIIM-141-A002 induces P-gp expression by 3-8 fold in LS-180 colon cancer cells at concentrations ranging from 12.5-100 µg/ml, respectively as shown in FIG. 5b, which might be the possible explanation for the increased efflux of Rh123 dye. Rifampicin was used as a positive control in this study. Rifampicin at 10 µg/mL showed 9-fold increase in the P-gp expression.

EXAMPLE 7

Inhibition of NLRP3 Inflammasome

THP-1 cells were differentiated with phorbol-12-myristate-13-acetate (PMA) (20 ng/ml) for 24 h. The media was changed after 24 h followed by rest of two days in complete RPMI containing 10% heat inactivated FCS. Cells were primed with LPS (1 µg/ml) for 4 h followed by pre-treatment with different concentration of hydroalcohlic extract of Crocus sativus for 30 min. Then, cells were stimulated with nigericin, 10 µM for 1 h. Supernatant was collected and stored at −20° C. for ELISA of IL-1β. Secretion of IL-1β with nigericin was measured by BD OptEIA for IL-1beta (human) and was considered as readout for NLRP3 activation.

IIIM-141-A002 showed strong inhibition of NLRP3 inflammasome at the low concentration of 25 µg/ml. Results are shown in FIG. 5c. IIIM-141-A002 at 100 µg/mL showed 42% inhibition of IL-1β release in comparison to LPS+nigericin (100%). MCC-950 (CAS no. 210826-40-7) was used as a positive control. MCC-950 at 40 ng/mL showed 90% inhibition of IL-1β release in comparison to LPS+nigericin (100%).

EXAMPLE 8

In-Vivo Efficacy of IIIM-141-A002 on Intra-Cerebroventricular Streptozotocin Induced Dementia in SD Rats Using Morris Water Maze Test Animals were randomized into 4 groups based on body weight, each group with n=5-7. Artificial cerebrospinal fluid (a CSF—147 mM NaCl, 2.9 mMKCl, 1.6 mM MgCl2, 1.7 mM CaCl2, 2.2 mM dextrose) was injected to group 1 or STZ (3 mg/kg) to group 2-5 animals through intra-cerebroventricular (ICV) route on day 1 and 3. On 15th-18th day, vehicle was administered to group 1-2, test compound IIIM-141-002 at a dose of 50 and 100 mg/kg, p.o. to group 3 and 4 animals respectively. Rats were subjected to MWM test 30 min after dosing, 4 trials were conducted each day for 4 days i.e. from 15th to 18th day. If animal failed to locate the hidden platform in stipulated time, they were gently pushed to the hidden platform and kept on platform for 20 seconds. Time (seconds) to locate the hidden platform was recorded as escape latency (latency time). Escape latency were recorded for retention session i.e. from day 16-18. The difference (% change) in escape latency was compared with aCSF.

Figure 6:
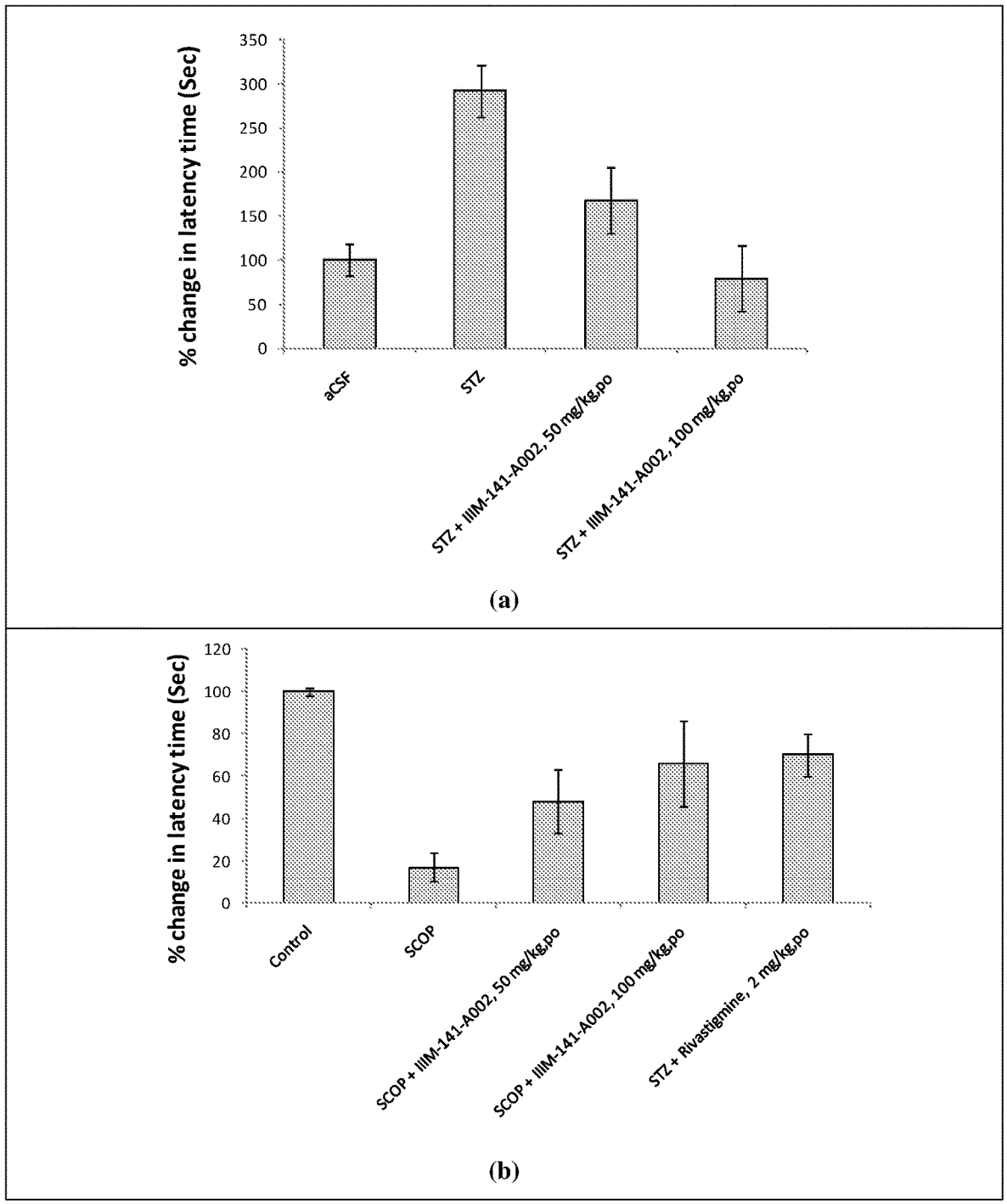

There was significant increase in latency time to locate the hidden platform in STZ treated rats as compared with aCSF treated rats suggesting memory impairment. A significant increase in latency time was observed in ICV-STZ treated rats at day 3 & 4 indicating memory deficit. Further, treatment with test compound (IIIM-141-002) decreased the STZ induced memory impairment in rats as demonstrated by reduction in latency time at dose of 100 mg/kg p.o. for 4 days. Results are shown in FIG. 6a.

EXAMPLE 9

In-Vivo Efficacy of IIIM-141-A002 on Scopolamine Induced Dementia in Swiss Albino Mice (SAM) Using Passive Avoidance Test Animals were randomized to their body weight (n=6-8). All animals were then habituated to experimental apparatus (Passive avoidance instrument of make—UGO Basile Biological Research Apparatus Italy) prior to the experiment. For habituation, animals were placed gently in the light compartment of the apparatus. After 5 seconds guillotine door was opened and animal allowed entering the dark compartment without giving the shock. Animals that took more than 100 seconds to enter the dark room were eliminated from the experiments. For acquisition trial the animals were placed in light compartment and allowed to enter the dark compartment through guillotine door. As soon as the animal entered to the dark compartment, door was closed and animal was delivered a foot shock (0.5 mA current) immediately for the duration of 5 seconds. Animals were then removed from apparatus after 20 seconds and placed temporarily in its home cage. Repeated the same procedure (keeping the gap between acquisition trials to 5 minutes) till the animal remained in the light compartment for consecutive 120 seconds. Retention was recorded at day 2 without shock in dark chamber. Increase in transfer latency time from light to dark chamber indicated learning in animals. Rivastigmine was used as positive control in this study. The data were acquired as transfer latency (in sec) i.e. time taken by each mice to move from light compartment to dark compartment (Table 2). Percentage (%) change in transfer latency as compared with control on retention trial was calculated. The scopolamine group was compared with control while test/standard groups were compared with scopolamine treated animals. For statistical analysis, one way ANOVA followed by Tukey test was used.

This study suggests that scopolamine administration results in memory impairment in mice as demonstrated by significant reduction in transfer latency as compared with control in retention trial. Administration of test compound IIIM-141-002 at 100 mpk for 7 day significantly recovered the memory as shown by increase in transfer latency as compared with scopolamine treated mice. Positive control rivastigmine at a dose of 2 mg/kg resulted in a significant reduction in latency time (FIG. 6b).

ADVANTAGES OF THE INVENTION

The main advantages of the present invention are:
1. The novel formulations provide sustained release of the active constituent (crocin-1) over the period of 24 hrs. resulting in reduced dosing frequency.
2. The novel formulations provide prolonged and steady plasma concentrations of *Crocus*-derived active constituent (crocin-1 and its active metabolite crocetin) over 24 hours and thus it can help avoid under-dosing between dosage intervals.
3. The novel formulations are free-flowing and non-hygroscopic.
4. The excipients/polymers used in the formulations are GRAS and are within the acceptable limits.
5. Extract of *C. sativus* is capable of inhibiting NLRP3 inflammasome.
6. Extract of *C. sativus* is capable of inducing P-gp, thus resulting in reduction in amyloid-beta load in the Alzheimer brains.

We claim:
1. A sustained release formulation comprising:
granules of a *Crocus sativus* extract or fraction comprising trans-crocetin di-(β-D-gentiohiosyl)ester (crocin-1) and one or more of trans-5-tG-crocin, cis-5-tG-crocin, trans-5-nG-crocin, cis-5-nG-crocin, trans-4-tG-crocin, cis-4-nG-crocin, trans-4-GG-crocin, trans-3-Gg-crocin, cis-3-Gg-crocin, trans-2-G-crocin, cis-2-G-crocin, trans-2-gg-crocin, cis-2-gg-crocin, trans-1-g-crocin, cis-1-g-crocin, cis-4-GG-crocin, cis-crocetin and trans-crocetin;
a hydroxypropyl methylcellulose or a combination of a hydroxypropyl methylcellulose and ethyl cellulose; and
optionally an excipient selected from a carrier, an adjuvant and a binder,
wherein a weight ratio of the granules of the *Crocus sativus* extract or fraction to the hydroxypropyl methylcellulose or the combination of a hydroxypropyl methylcellulose and ethyl cellulose is in a range of 30:70 to 70:30, and
wherein a total in-vitro dissolution time of the sustained release formulation required for release of 60-80% of crocin-1 is between 8 to 16 hours.

2. The sustained release formulation as claimed in claim 1, wherein said extract is a hydroalcoholic extract.

3. The sustained release formulation as claimed in claim 1, wherein the fraction is an aqueous fraction of a water/ethyl acetate system.

4. The sustained release formulation as claimed in claim 2, wherein the hydroalcoholic extract contains at least 15% w/w of crocin-1.

5. The sustained release formulation as claimed in claim 3, wherein the fraction contains at least 30% w/w of crocin-1.

6. The sustained release formulation as claimed in claim 1, wherein the hydroxypropyl methylcellulose is hydroxypropyl methylcellulose K4M (HPMC-K4M) or hydroxypropyl methylcellulose K15M (HPMC-K15M).

7. The sustained release formulation as claimed in claim 1, wherein said formulation is in the form of a hard gelatin capsule.

8. The sustained release formulation as claimed in claim 1, wherein the formulation comprises an extract of *Crocus sativus* in an amount of 30-70% by weight of the formulation and at least 4.5% of crocin-1.

9. The sustained release formulation as claimed in claim 1, wherein the binder is selected from group consisting of polyvinylpyrrolidone K30 and polyvinylpyrrolidone K15.

10. The sustained release formulation as claimed in claim 1, wherein the formulation is in the form of a tablet.

11. The sustained release formulation as claimed in claim 1, wherein the *Crocus sativus* extract or fraction comprises trans-5-nG-crocin, trans-4-GG-crocin, trans-3-Gg-crocin, cis-3-Gg-crocin, trans-2-gg-crocin, and cis-4-GG-crocin.

12. The sustained release formulation as claimed in claim 11, wherein the *Crocus sativus* extract contains 33.11±3.25% trans-4-GG-crocin.

13. The sustained release formulation as claimed in claim 11, wherein the *Crocus sativus* fraction contains 55.19±1.82% trans-4-GG-crocin.

14. The sustained release formulation as claimed in claim 1, wherein the formulation is non-hygroscopic.

15. The sustained release formulation as claimed in claim 7, wherein the hard gelatin capsule has 50 mg of crocin-1.

* * * * *